US008322853B2

(12) United States Patent
Marshall et al.

(10) Patent No.: US 8,322,853 B2
(45) Date of Patent: Dec. 4, 2012

(54) DIAGNOSTIC METHOD AND APPARATUS FOR PREDICTING POTENTIAL PRESERVED VISUAL ACUITY

(75) Inventors: John Marshall, Farnborough (GB); Lucia Pelosini, Petts Wood (GB)

(73) Assignee: Optos PLC (GB)

( * ) Notice: Subject to any disclaimer, the term of this patent is extended or adjusted under 35 U.S.C. 154(b) by 297 days.

(21) Appl. No.: 12/572,489

(22) Filed: Oct. 2, 2009

(65) Prior Publication Data

US 2011/0080558 A1    Apr. 7, 2011

(51) Int. Cl.
A61B 3/10    (2006.01)
A61B 3/14    (2006.01)
A61B 3/00    (2006.01)

(52) U.S. Cl. .................... 351/206; 351/205; 351/246

(58) Field of Classification Search .................. 351/205, 351/206, 221, 246
See application file for complete search history.

(56) References Cited

U.S. PATENT DOCUMENTS

| | | | |
|---|---|---|---|
| 6,431,707 B1 * | 8/2002 | Jordan et al. ................. | 351/200 |
| 2007/0216909 A1 | 9/2007 | Everett et al. | |
| 2008/0309881 A1 | 12/2008 | Huang et al. | |
| 2009/0244485 A1 | 10/2009 | Walsh et al. | |

OTHER PUBLICATIONS

Markomichelakis, Nikos N. et al, "Patters of Macular Edema in Patients with Uveitis," Ophthalmology, May 1, 2004, pp. 946-953, vol. III, No. 5, Elsevier Inc.
Pelosini, L. et al, "Optical Coherence Tomography may be used to Predict Visual Acuity in Patients with Macular Oedema," Jun. 10, 2010, pp. 1-28, IOVS.
Witkin, Andre J. et al, "High-speed Ultrahigh Resolution Optical Coherence Tomography before and after Ranibizumab for Age-related Macular Degeneration," Ophthalmology, May 1, 2009, pp. 956-963, vol. 116, No. 5, Elsevier Inc.
Ko, Tony H. et al, "Comparison of Ultrahigh- and Standard-Resolution Optical Coherence Tomography for Imaging Macular Pathology," Ophthalmology, Nov. 1, 2005, pp. 1922.e1-1992.e15, vol. 112, No. 11, Elsevier Inc.

* cited by examiner

*Primary Examiner* — Ricky Mack
*Assistant Examiner* — Mahidere Sahle
(74) *Attorney, Agent, or Firm* — Laubscher & Laubscher, PC

(57) ABSTRACT

A diagnostic method is disclosed wherein the potential preserved visual acuity in the retina of a patient is determined from the amount of tissue connecting the inner and outer plexiform layers remaining in the retina.

26 Claims, 9 Drawing Sheets

DIAGNOSTIC METHOD AND APPARATUS FOR PREDICTING POTENTIAL PRESERVED VISUAL ACUITY

FIELD OF THE INVENTION

This invention relates to the field of ophthalmology, and in particular to a diagnostic method and apparatus for predicting potential preserved visual acuity in patients with impaired vision.

BACKGROUND OF THE INVENTION

There are many reasons for patients to incur visual impairment, and in such cases it is important for the ophthalmologist to be able to determine the visual function and predict the visual outcome after treatment. For example, it would be futile for a patient to undergo surgical intervention if the condition of the retina is such that no possibility of improvement exists.

One common cause of visual impairment is macular oedema. Macular oedema results from abnormal accumulation of fluid in the central retina and indicates compromised function in one or both of the blood retinal barriers. It is a common sequel of many ocular conditions and the main cause of visual loss in diabetic retinopathy.

Any abnormal pooling of extracellular fluid may result in displacement of the spatial relationships between retinal neuronal components. Small amounts of fluid may lead to an increase in overall retinal thickness, whilst larger amounts may give rise to cell free spaces as seen in cystoid macular oedema It is known to predict visual acuity by measuring macular thickness. However, qualitative analysis of data describing the relationship between central macular thickness (CMT) and visual acuity shows that the correlation between CMT and visual acuity is only moderate that CMT is only able to predict 16.6% of visual acuity.

SUMMARY OF THE INVENTION

It is an object of the invention to provide a method of predicting potential visual acuity with improved performance.

According to the present invention there is provided a diagnostic method wherein the potential preserved visual acuity in the retina of a patient is determined from the amount of tissue connecting the inner and outer plexiform layers remaining in the retina.

The inventors have shown that there is a good correlation between the amount of remaining tissue connecting the inner and outer plexiform layers and potential visual acuity. The reason for this correlation is believed to be that the retinal tissue within these layers provides axonal connections within the retina between the photoreceptors and ganglion cells, and the measure of preserved axonal connections is a good indicator of preserved visual acuity.

In one embodiment, a series of coronal images are taken at different distances from the fovea. These provide a series of concentric rings (which may or may not be circular) of different radii surrounding the fovea. The amount of tissue remaining between the plexiform layers computed from an analysis of the image dataset. The inventors have found that connecting tissue in the region between about 1000-2000 microns from the fovea is the most effective predictor of preserved visual acuity.

The plane in which the measurements are taken may be the minimum detectable plane between the inner and outer plexiform layers. In this context, it will be understood that the term plane is used to define a layer having a finite thickness following a planar contour.

The plane in which the measurements are taken may be shaped to follow the contour of a predefined surface, such as the retinal surface or retinal pigment epithelium layer.

Additionally, the level of visual acuity can be determined from an analysis of the sizes, for example the minimum sizes, of Muller fibers and/or bipolar cells connecting the inner and outer plexiform layers.

The measurements are preferably taken with a suitable imaging and processing system such as Optical Coherence Tomography (OCT), ultrasound, or confocal. A preferred system uses a combined OCT/confocal system that allows the OCT and confocal images to be displayed with a pixel for pixel correspondence on a computer screen.

In another aspect the invention provides a diagnostic apparatus for determining the potential preserved visual acuity in the retina of a patient, comprising an imaging system for imaging the retinal tissue between the inner and outer plexiform layers; and a processor for computing the potential preserved visual acuity based on the amount of said retinal tissue remaining between said inner and outer plexiform layers.

The processor may select the layer and position to measure the amount of connecting tissue automatically, and may make an indirect measurement of the amount of tissue connecting the inner and outer plexiform layers.

BRIEF DESCRIPTION OF THE DRAWINGS

The invention will now be described in more detail, by way of example only, with reference to the accompanying drawings, in which:—

DETAILED DESCRIPTION OF THE INVENTION

Figure 1:
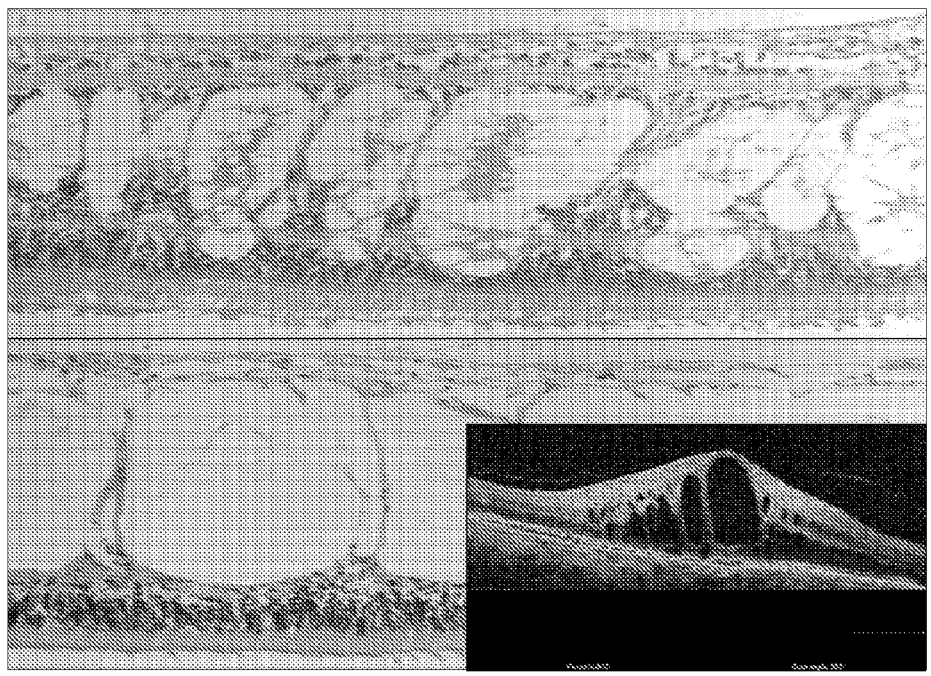
FIG. 1 shows light microscopy and optical coherence tomography images of a human retina affected by cystoid macular oedema (CMO).
Figure 2:
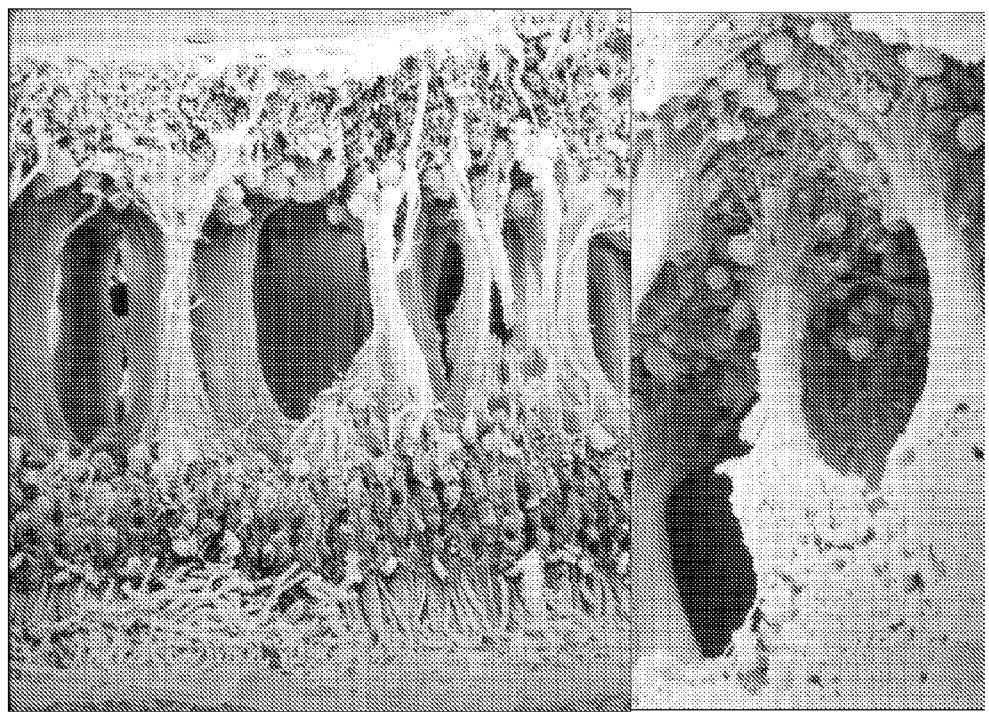
FIG. 2 is a scanning electron microscopy image of cystoid macular oedema.

Observations from histology and optical coherence tomography (OCT), as shown in FIG. 1, give a false impression of multiple cysts delineated by tissue structures in the Z-plane of the retina. However, scanning electron microscopy, as shown in FIG. 2, shows that more commonly a single cystic space is present within which a number of structures extend from the inner to the outer retina. Such structures consist of columns of Muller's fibers together with the axonal elements of bipolar cells passing between the two plexiform layers. Empirical studies have demonstrated that the two plexiform layers together with the outer limiting membrane form a physical resistance barrier to fluid movements. Thus, extracellular fluid may be contained within layers defined by these resistance barriers. In diabetic retinopathy, cystic spaces may occur either between the inner and the outer plexiform layers or between the outer limiting membrane and the outer plexiform layer. In the former location, there is a potential to displace bipolar cells leading to cell loss or compromised function, while in the latter, only photoreceptor cells are at risk.

Given the fundamental role of bipolar cells as the sole communication pathway between photoreceptors and ganglion cells, any loss of connectivity between these cells will compromise visual function. It therefore follows that the more the retinal thickness increases, the more such axons will be stretched. As a consequence some will break. This phenomenon is believed to explain the mechanism underlying the apparent relationship between increasing retinal thickness and decreasing visual acuity.

By contrast, those bipolar cells whose axons are closely adjacent to Muller's fibers will have a greater chance of surviving displacement because of the greater physical strength and support provided by the adjacent Muller's fibers.

The inventors have shown that a useful indicator of the visual acuity and potential visual outcome in eyes with macular oedema is to analyze the residual volume of tissue passing between the two plexiform layers, as only such areas would allow passage of bipolar axons between photoreceptors and ganglion cells. The impact of photoreceptor-ganglion cell connectivity on visual acuity further depends upon the location of surviving axons within the central visual field. An optimal measurement of potential function would be an evaluation of the number of vertical elements passing between the plexiform layers, their diameter and eccentricity from the fovea.

Experimental Results

Patients with macular oedema were prospectively recruited from both diabetic and uveitic outpatient clinics over a period of nine months. The study involved a baseline assessment of visual function, ophthalmoscopy and OCT imaging at a single timepoint. Patient information was anonymized at the time of patient recruitment to allow independent data analysis.

Inclusion criteria for the study were a clinical diagnosis of cystoid macular oedema (CMO), confirmed either by OCT alone or by OCT and fundus fluorescein angiography (FFA) at the time of enrolment. For each patient either one or both eyes were included in the study.

Patients with coexisting ocular pathologies were excluded. Exclusion criteria included the presence of media opacity affecting the quality of the OCT scan and angiographic or clinical evidence of ischaemic maculopathy.

Each patient underwent a complete anterior segment examination by slit-lamp biomicroscopy and best corrected visual acuity assessment using a LogMAR chart at 3 meters distance. All patients were then dilated using Phenylephrine 2.5% and Tropicamide 1% and examined by indirect fundoscopy with a 78D lens. In the diabetic patients, fluorescein angiography was required as one of the inclusion criteria of the study in order to assess retinal circulation and to allow exclusion of patients with subclinical foveal ischaemia.

Figure 9:
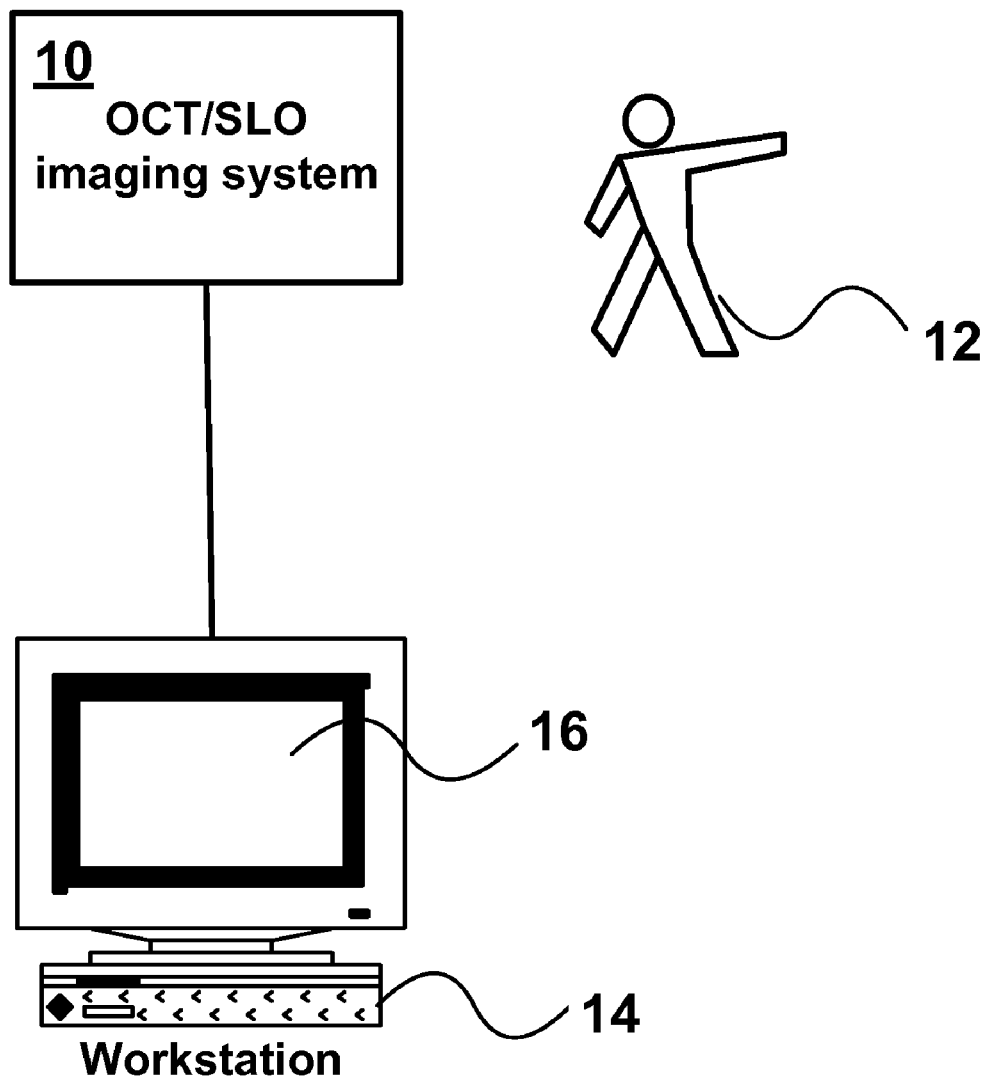
FIG. 9 is a schematic illustration of the apparatus for determining the potential preserved visual acuity in a retina of a patient according to the invention.

Optical coherence tomography was carried out using a Spectrum-OTI spectral domain OCT/SLO system (Spectral OCTSLO model E, Spectrum-Ophthalmic Technologies Inc., Toronto, Canada). This device is an optical imaging system, combining a Confocal Scanning Ophthalmoscope and Optical Coherence Tomography. Both the confocal fundus SLO image and the OCT image are generated through the same optics and displayed simultaneously on the computer screen with pixel to pixel correspondence. The system uses light generated from an infrared broadband super luminescent diode (SLD) with a wavelength between 790 nm and 950 nm. Cross-sectional images of the retina along the x-y plane (B-Scan), such as single line, radial and raster scans, could be obtained as well as coronal images within the z plane (C-scan). The setup is shown in FIG. 9, where the OCT/SLO unit 10 was used to image the eye of patient 12. The results were processed in computer 14 and displayed on screen 16.

A state of the art Fourier domain OCT device, such as described above, and designed for ophthalmic use can typically capture axial data over 2 mm in depth (measured in air) at 20,000 lines per second. The scan pattern across the retina can be arranged in a grid of 200 by 200 points with a spacing between lines and rows of around 25 microns. This scan pattern is centered on the fovea with a capture time of 2 seconds. The imaging depth is defined by several parameters, but the useful depth for use in this analysis is at least 1.5 mm measured in air.

Automated methods to adjust for patient movement during acquisition can be employed on the dataset prior to analysis. This can make use of the fast acquisition and small spacing between lines and rows, but can take the form of other simultaneous acquisition streams.

Analysis of the 3D dataset is achieved by segmenting the dataset through the retina in the coronal plane to view tissue present at a level between the inner and outer plexiform layers of the retina. In this embodiment the segmentation thickness would be around 10 microns (the resolution of the system in the axial direction).

From this segmented view (image), the image is processed to a 2 bit image so that each pixel is either turned into a one or zero (where a one would be tissue and a zero, none or oedema). The amount of remaining tissue within a 1 mm radius of the anatomical fovea is measured and this used as a predictor of the visual acuity that could be potentially achieved after treatment and resolution of the oedema.

In preliminary studies, scans were obtained using three different modes of operation. First, a series of 24 radial scans over 360 degrees were automatically initiated intersecting at the centre of the patient's fixation. Secondly, a single scan mode was selected whose orientation and location within the fundus was determined by the operator. Thirdly, the system was used to generate a raster scan of the macula from the superior to the inferior arcade with 64 scans, again centred by the patient's fixation.

Figure 3A:
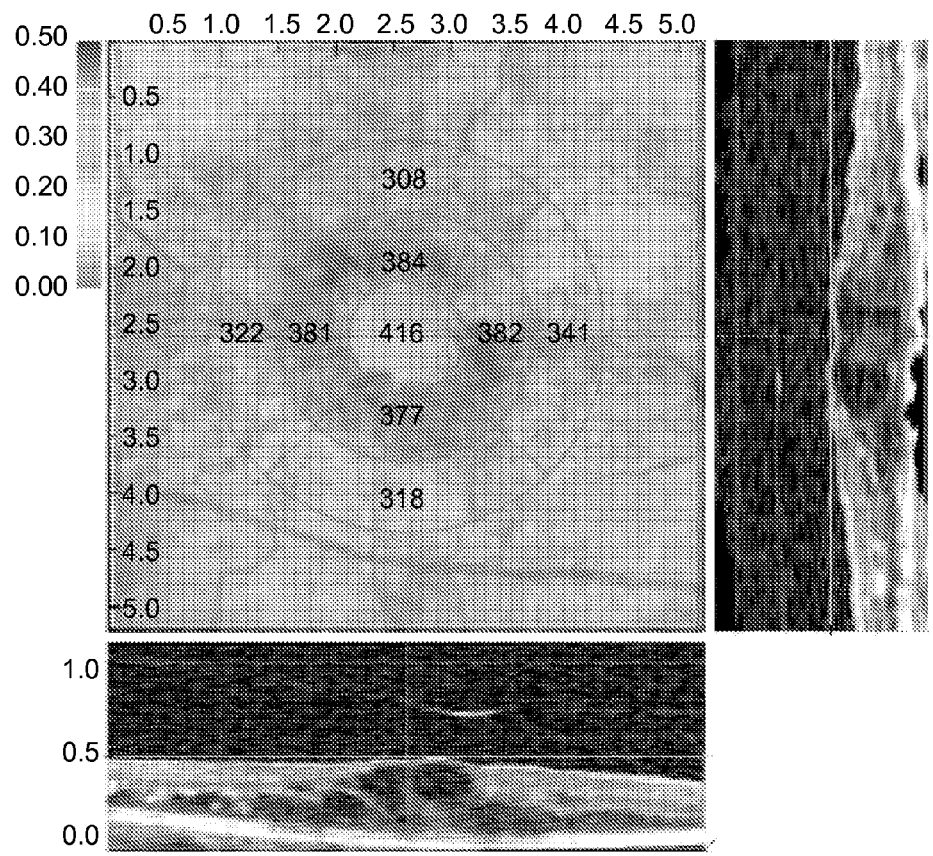
FIG. 3A is a macular thickness map of a patient with macular oedema representing subfield mean thicknesses as from ETDRS study.

Three dimensional views of the macula were obtained by selecting the topography mode where images were viewed as surface maps and these were extracted manually by slicing the 3-D picture using the device based image analysis software. The topography scan also allowed the operator to extract information about retinal thickness in different areas of the posterior pole by using the ETDRS macular grid. Coronal scans (C-scans) were fundamental to the present study and obtained by selecting the mid point between the ganglion cell layer and the innermost aspect of the outer plexiform layer, in most cases to mid depth of the cysts. In practice this was obtained by adjusting the section plane to an appropriate level parallel with the retinal surface in the B scan displayed on the x-axis of the coronal image (FIG. 3A).

Figure 3B:
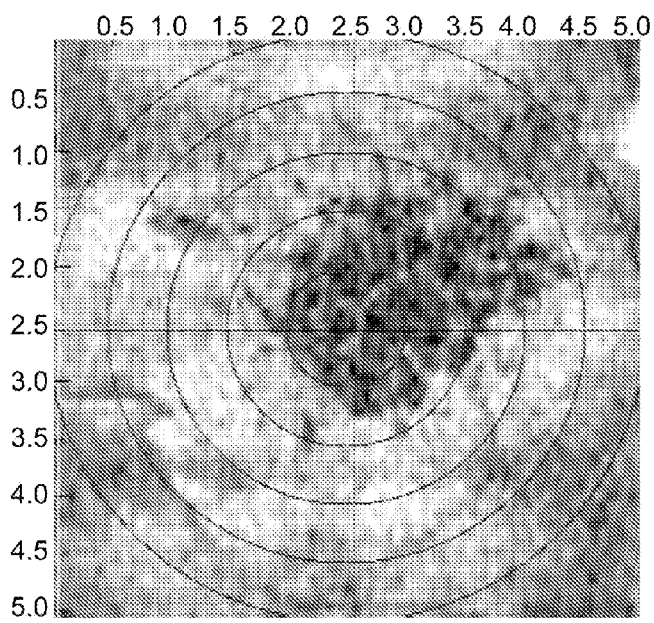
FIG. 3B is a grayscale coronal OCT scan with superimposed grid dividing the macula in 5 areas of increasing eccentricity (radii: 500μ, 1000μ, 1500μ, 2000μ, 2500μ).
Figure 4A:
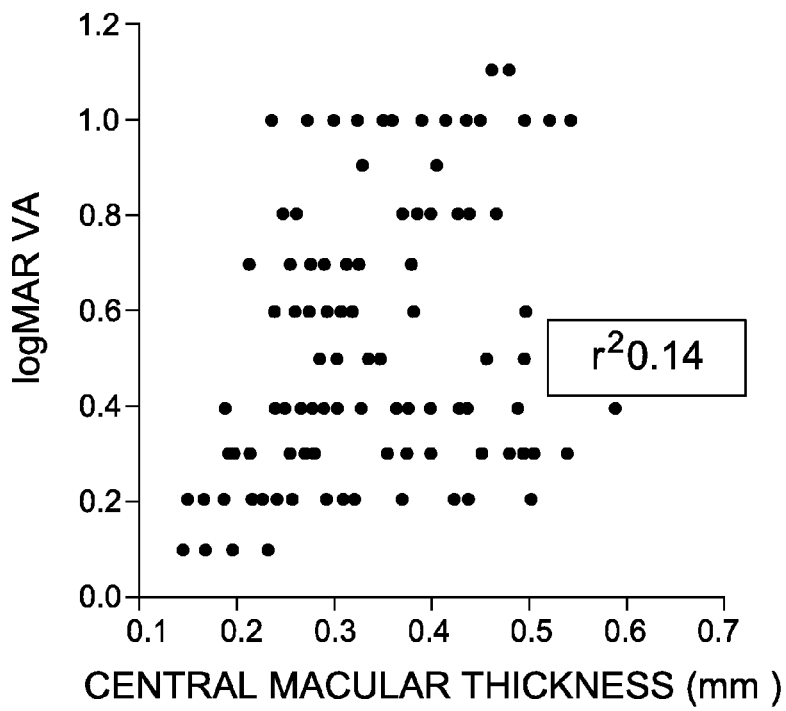
FIG. 4 shows scatter plots of the relationship between a) Central macular thickness versus LogMAR VA (rs=0.407*); b) Tissue integrity within circle 1 versus LogMAR VA (rs=−0.832*); c) Tissue integrity within circle 2 versus LogMAR VA (rs=−0.841*); d) Tissue integrity within circle 3 versus LogMAR VA (rs=−0.624*); e) Tissue integrity within circle 4 versus LogMAR VA (rs=−0.277*); and f) Tissue integrity within circle 5 versus LogMAR VA (rs=−0.134*).
Figure 4B:
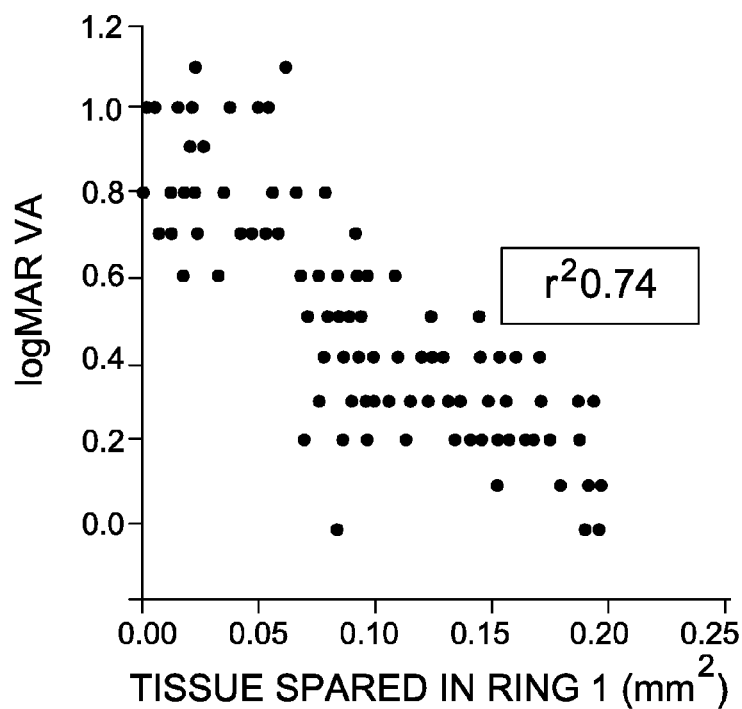
Figure 4C:
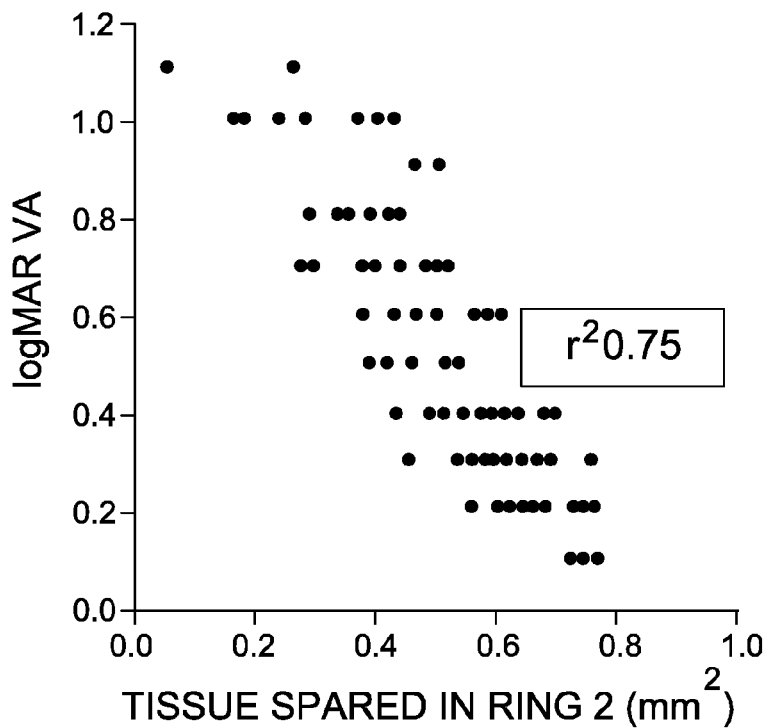
Figure 4D:
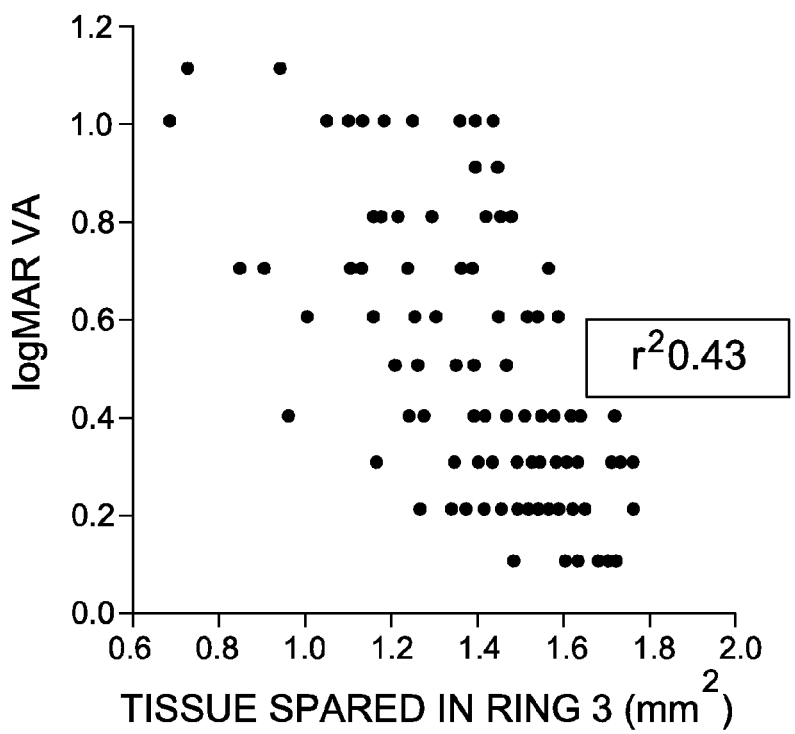
Figure 4E:
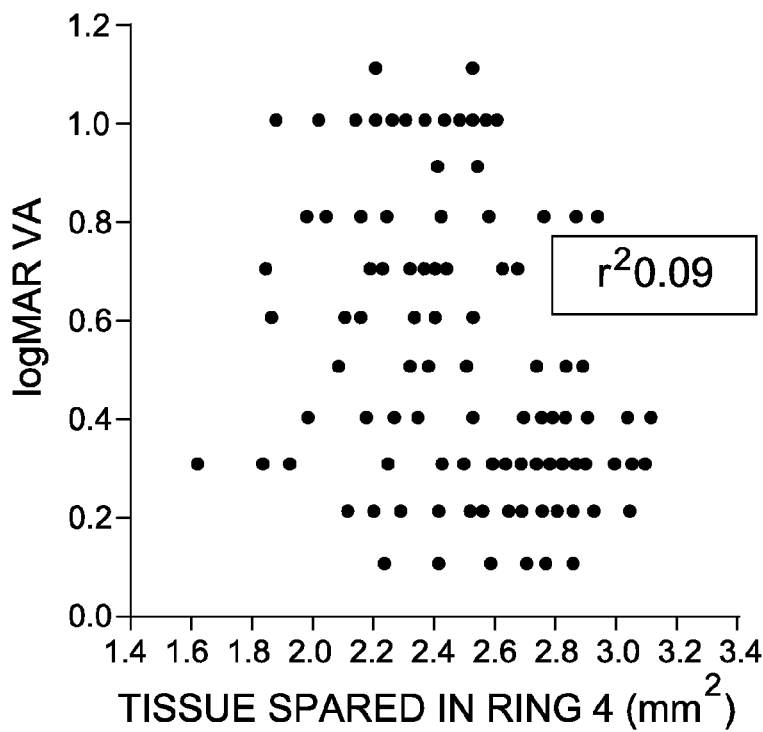
Figure 4F:
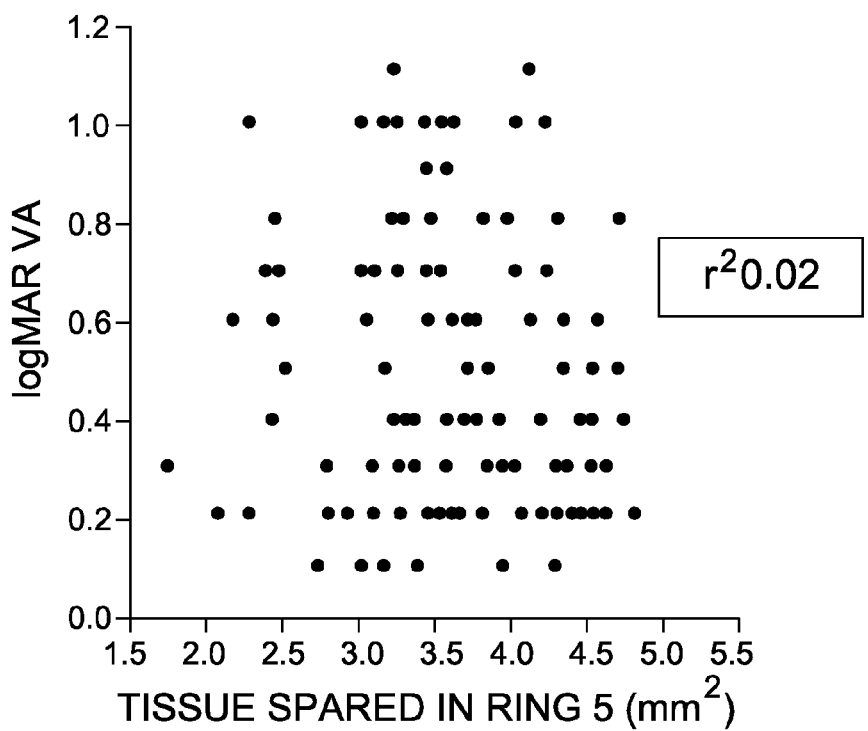

The image analysis system extracted three datasets, namely 1) the number of columns of tissue present 2) their cross-sectional area at their narrowest point 3) and their eccentricity from the foveal centre. Data were collected from a series of concentric rings of 500 μm, 1000 μm, 1500 μm, 2000 μm, 2500 μm radii respectively (FIG. 3B). Within each ring, the area of surviving tissue as opposed to cystic space was extracted by first processing the data to compress the grayscale such that tissue became white and the oedema black.

Next, the data were processed to count the number of white pixels present within each ring, thus giving a measure proportionate to the potential number of connections passing between the two plexiform layers. The number of pixels of spared tissue within each annulus was converted to an area in $mm^2$ by scaling the ratio of the number of pixels of spared tissue to the total number of pixels in the annulus by the area in $mm^2$ of the annulus.

This study had three primary outcomes: 1) Best corrected Log MAR visual acuity; 2) retinal tissue integrity evaluated as number of pixels corresponding to the tissue component between cystic spaces and observable at increasing eccentricities from the fovea in segmented images of OCT/SLO coronal scans; and 3) central macular thickness measurement obtained from the OCT/SLO retinal thickness map.

A linear regression model was developed to assess if the amount of glia could be used to predict visual acuity. A data set of 129 eyes were randomized and split into two data sets, one of 100 eyes and the other of 29 eyes.

The first group of 100 eyes was used to determine the linear regression model. The remaining 29 eyes were used to test the validity of the model in predicting visual acuity. All outcome variables were entered into a stepwise linear regression model with logMAR visual acuity as the outcome variable. Log-MAR is a commonly used scale for measuring visual acuity.

The criterion for entry into the model was P=0.05 and P=0.10 for removal. Stepwise linear regression is an extension of simple linear regression where the dependent variable is predicted by a linear equation involving one outcome or independent variable and a constant. In stepwise linear regression, multiple variables can be linearly combined in the model. They are entered automatically by the statistics software provided they make a statistically significant improvement in the model.

The remaining 29 eyes were used to test the model by assessing the agreement between the predicted and measured visual acuity using the Bland-Altman method. A total of 81 participants enrolled, 36 males and 45 females. The average age was 63 years (range 26-87 years).

Most patients (73%, 59 subjects) underwent fluorescein angiography, whereas in the remaining group an angiographic study could not be performed (27%, 22 subjects) due to previously documented adverse reaction to the dye (9 subjects), refusal to the investigation (8 subjects) or technical difficulty to obtain a satisfactory venous access (7 subjects). Typical patient contact time was 40 minutes of which only 5 minutes were required for OCT imaging.

The distribution of spared retinal tissue values in the concentric annuli varied with eccentricity. Tissue integrity date in ring 1, 2 and 3 were not normally distributed (p=0.001; 0.001; and 0.02 respectively), whereas data related to tissue integrity within rings 4 and 5 displayed a normal distribution (p=0.093 and p=0.2, respectively). Values for central macular thickness showed a normal distribution (p=0.059), whereas LogMAR visual acuity values were not normally distributed. The relationship between tissue integrity at increasing eccentricity and LogMAR visual acuity was significant at the 0.01 level (2 tailed) in circles 1 (r=0.832), 2 (r=0.841), 3 (R=0.624), 4 (R=0.277). The correlation was significant at 0.05 level (2 tailed) in ring 5 (r=0.152).

Qualitative analysis of the data shows a clear linear relationship between the amount of spared tissue within rings 1 and 2 and Log MAR visual acuity. The relationship between spared tissue in ring 3 and visual acuity was less clear and became even less apparent in rings 4 and 5 (FIG. 4).

The linear regression model demonstrated that measures of tissue integrity derived from rings 1 and 2 predicted up to 74% and 75% of visual acuity respectively. The $r^2$ values for rings 3, 4 and 5 were significantly lower as shown in the following table.

TABLE

| Variable | R | P (2 tailed) | R2 % | R2 |
|---|---|---|---|---|
| CMT | 0.047 | <0.001 | 16.6% | 0.14 |
| Tissue spared in ring 1 (500μ) | −0.832 | <0.001 | 69.2% | 0.74 |
| Tissue spared in ring 2 (1000μ) | −0.841 | <0.001 | 70.7% | 0.75 |
| Tissue spared in ring 3 (1500μ) | −0.624 | <0.001 | 38.9% | 0.43 |
| Tissue spared in ring 4 (2000μ) | −0.277 | 0.001 | 7.7% | 0.09 |
| Tissue spared in ring 5 (2500μ) | −0.133 | 0.132 | 1.8% | 0.092 |

Comparative Example

Figure 5:
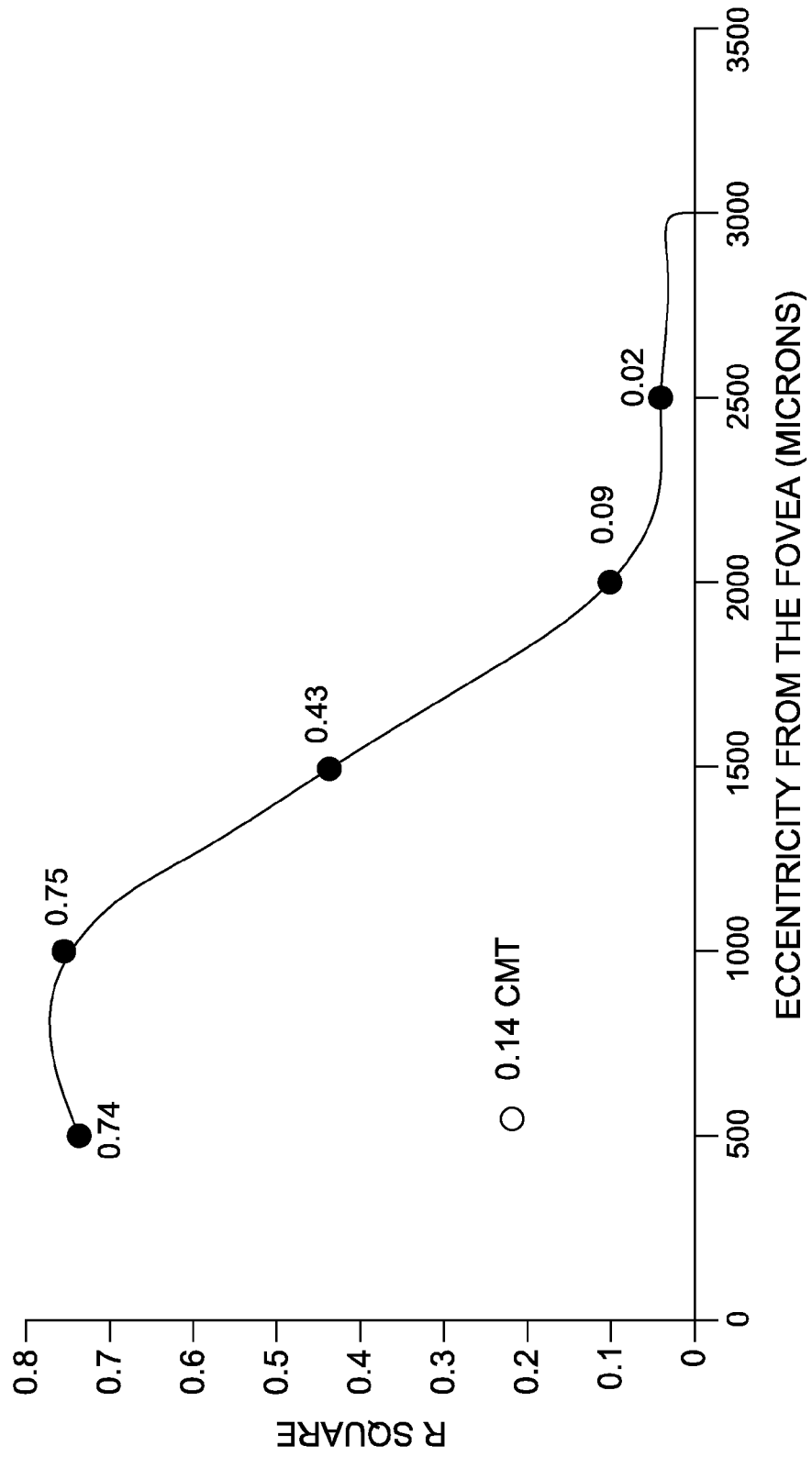
FIG. 5 shows the variation in R2 values representing the association between visual acuity and retinal spared tissue at increasing eccentricity as well as visual acuity and central macular thickness (CMT)

The scatter plots shown in FIG. 5 represent the relationship between central macular thickness and visual acuity (a) and between spared retinal tissue at increasing eccentricities and visual acuity (b-f) for all 129 eyes.

Qualitative analysis of data describing the relationship between central macular thickness (CMT) and visual acuity showed a very weak link as shown in FIG. 5. The correlation between CMT and LogMAR visual acuity was moderate (r=0.407). The regression analysis of CMT versus visual acuity demonstrates that CMT predicts only 16% of visual acuity.

The linear regression model was given by $$\log MAR = 1.089 + 0.252 \times CMT - 2.140 \times T1 - 0.854 \times T2 \quad (1)$$

where CMT is the central macular thickness in mm and T1 and T2 are the areas of tissue sparing in $mm^2$ in rings 1 and 2 respectively. This model has an $R^2$ value of 80.7% indicating that equation (1) explained over 80.7% of the variation in LogMAR visual acuity. It was noteworthy that the most predictive variable was T2 and this alone could predict 74.4% of the variation in LogMAR visual acuity.

Figure 6:
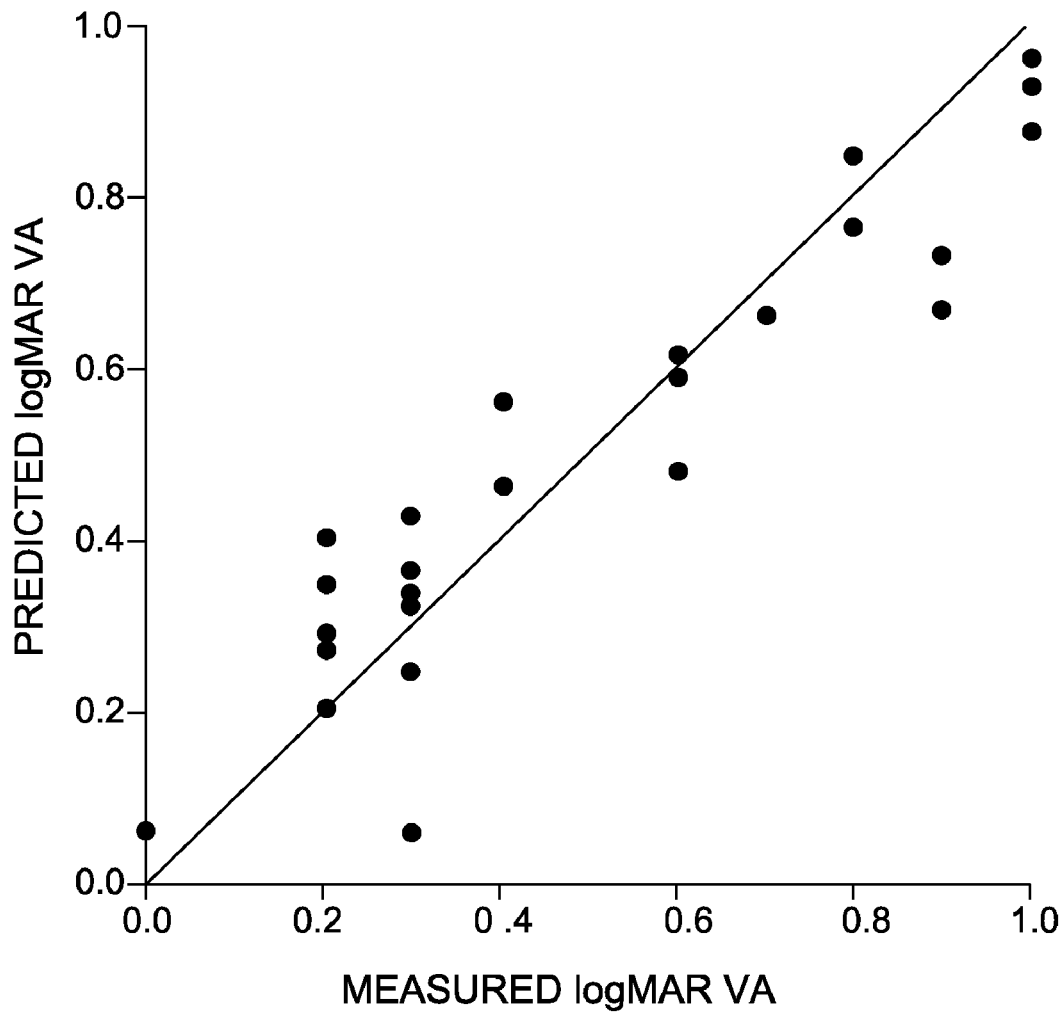
FIG. 6 is a scatter plot, with line of equality, for measured versus predicted LogMAR visual acuity using the linear regression model.

FIG. 6 shows a scatter plot of the measured Log MAR visual acuity plotted against the estimated LogMAR visual acuity. A line of equality is shown along which all data points would be expected to lie in presence of perfect agreement. This was not the case, as would be expected from most clinical measures.

Figure 7:
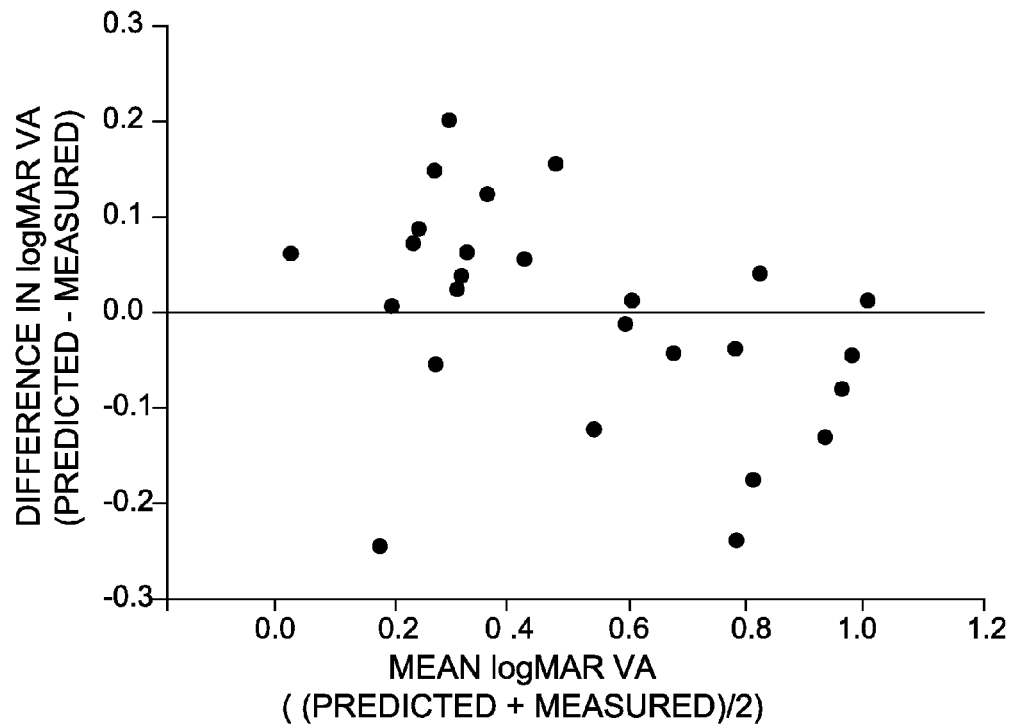
FIG. 7 is a Bland-Altman mean-difference plot demonstrating agreement between measured and predicted LogMAR visual acuity.

FIG. 7 shows the Bland-Altman mean-difference plot for the data. It shows that there is a relationship between the mean LogMAR visual acuity and the differences ($r=-0.44$; $P=0.016$). This means that the bias changes with visual acuity and that the limits of agreement will be underestimated for good visual acuity (small values of LogMAR visual acuity) and overestimated for poor visual acuity (high values of LogMAR visual acuity).

Figure 8:
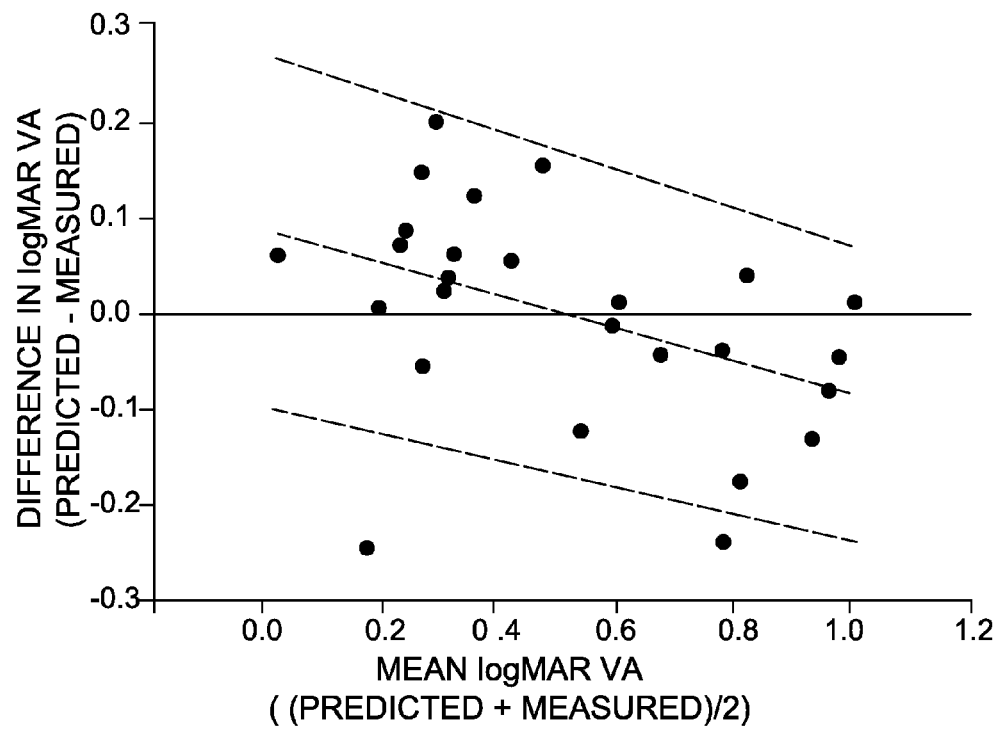
FIG. 8 is a Bland-Altman mean-difference plot showing bias (solid line) and upper and lower limits of agreement (dashed line)

FIG. 8 shows the change in bias and limits of agreement with mean LogMAR acuity. A more accurate value for the limits of agreement is $\pm 0.17$ log units at a LogMAR visual acuity of 0.5 although this changes slightly with the mean measured value.

The above results also demonstrate that there is a strong correlation between visual acuity in patients with cystoid macular oedema and the volume of tissue passing between the two plexiform layers in the central retina as determined by OCT. It is the first time that a predictive measure of visual performance has been derived from imaging of macular oedema.

The results demonstrate that good visual acuity only occurred in those patients with an adequate volume of tissue running between the inner and the outer plexiform layers in the central 1000-2000µ of retina (FIGS. 4 and 5). Given that foveal cones have inner connecting fibers that may be up to 500 µm in length, foveolar cones may connect to bipolar cells displaced 500 µm radially from the inner and outer segments. Thus this lateral displacement of connections between foveal cones and ganglion cells explains the dependency of visual acuity on the tissue integrity in both rings 1 and 2.

While there was still reasonable correlation within ring 3, which is believed to be due to signals derived from photoreceptors at the extreme edges of the fovea, correlation was lost within rings 4 and 5. In these locations, although large amounts of tissue volume may be spared, the connectivity is predominantly with extrafoveal photoreceptors.

From the linear regression model, it appears that a minimum of 50% of preserved retinal tissue within ring 1 is necessary in order to maintain a visual acuity of 0.4 LogMAR or better (FIG. 4, scatter plot b), whereas at least 70% of the retinal tissue within ring 2 is necessary for a level of visual acuity of 0.4 LogMAR or better (FIG. 4, scatter plot c).

Even though the total number of bipolar axons traversing the space between the plexiform layers may be significantly reduced, both horizontal and amacrine cells will contribute to image processing and VA by integrating signals over a number of photoreceptor cells and ganglion cells respectively.

The apparent correlation between the increase in retinal thickness and the decrease in visual acuity in accordance with prior art methods may be explained by the present results whereby increase in thickness will be associated with increase in loss in viable axons. The more direct approach to assessing neuronal survival in the present invention would also explain why the correlation values are so much better.

The above results establish retinal tissue integrity as a measure of preserved axonal connections and indicator of visual function. The strength of the relationship between preserved tissue and visual function, as expected, decreases at increasing eccentricities from the centre of the fovea.

The ability to determine the potential visual outcome for patients prior to the commencement of any treatment trial is highly beneficial in that it will allow exclusion of those individuals who could not in anyway benefit from intervention.

It will be appreciated that the invention could be implemented in software, and as such the invention also extends to a computer program product comprising a storage medium having stored thereon instructions which when executed on a general purpose computer process a dataset obtained from a 3D ophthalmic imaging system, such as an OCT/confocal system, to derive therefrom the amount of tissue connecting the inner and outer plexiform layers remaining in the retina.

The invention claimed is:

1. A method of determining the potential preserved visual acuity in a retina of a patient, the method comprising:
   using an imagery system to create an images dataset representing the amount of tissue connecting the inner and outer plexiform layers in the retina;
   measuring the amount of tissue connecting the inner and outer plexiform layers in the retina from the images dataset;
   processing the measured amount of tissue to determine if the measured amount of tissue is within a predetermined range; and
   if the amount of tissue measured is within the predetermined range, displaying an image representing the presence of visual acuity in the retina of the patient.

2. The method as claimed in claim 1, wherein said dataset includes measurements of the amount of tissue between the outer plexiform layers and the external limiting membrane.

3. The method as claimed in claim 2, wherein said dataset comprises measurements made in a series of concentric rings of different radii surrounding the fovea.

4. The method as claimed in claim 1, wherein said amount of said tissue is determined in a region lying between 1000 and 2000 microns from the fovea.

5. The method as claimed in claim 1, wherein the plane in which the measurements are taken is the minimum detectable between the inner and outer plexiform layers.

6. The method as claimed in claim 1, wherein the plane in which the measurements are taken is shaped to follow the contour of a predefined surface.

7. The method as claimed in claim 1, wherein said predefined surface is the retinal surface or retinal pigment epithelium layer.

8. The method as claimed in claim 1, wherein the level of visual acuity is determined from an analysis of the sizes of Muller fibers and/or bipolar cells connecting the inner and outer plexiform layers.

9. The method as claimed in claim 1, wherein said imaging system is a three-dimensional imaging system.

10. The method as claimed in claim 9, wherein said three dimensional imaging system is a combined OCT/confocal imaging system.

11. The method as claimed in claim 1, wherein the potential preserved visual acuity is computed by processing said dataset in accordance with a predetermined algorithm.

12. An apparatus for determining the potential preserved visual acuity in a retina of a patient, the apparatus comprising:
   an imagery system for creating an images dataset representing the amount of tissue connecting the inner and outer plexiform layers in the retina and for measuring the amount of tissue connecting the inner and outer plexiform layers in the retina from the images dataset;
   a processor for determining if the measured amount of tissue is within a predetermined range; and
   a display for displaying an image representing the presence of visual acuity in the retina of the patient, if the amount of tissue measured is within the predetermined range.

13. The apparatus as claimed in claim 12, wherein said processor is programmed to create the dataset at different distances from the fovea.

14. The apparatus as claimed in claim 13, wherein said dataset includes measurements of the amount of tissue between the outer plexiform layers and the external limiting membrane.

15. The apparatus as claimed in claim 13, wherein said dataset comprises measurements made in a series of concentric rings of different radii surrounding the fovea.

16. The apparatus as claimed in claim 12, wherein said processor determines the amount of said tissue in a region lying between 1000 and 2000 microns from the fovea.

17. The apparatus as claimed in claim 12, wherein said imaging system is configured to take measurements in the plane which is the minimum detectable between the inner and outer plexiform layers.

18. The apparatus as claimed in claim 12, wherein the plane in which the measurements are taken is shaped to follow the contour of a predefined surface.

19. The apparatus as claimed in claim 18, wherein said predefined surface is the retinal surface or retinal pigment epithelium layer.

20. The apparatus as claimed in claim 12, wherein said processor is programmed to determine the level of visual acuity from an analysis of the sizes of Muller fibers and/or bipolar cells connecting the inner and outer plexiform layers.

21. The apparatus as claimed in claim 20, wherein said three dimensional imaging system is a combined OCT/confocal imaging system.

22. A computer program product comprising a storage medium having stored therein instructions for determining the potential preserved visual acuity in a retina of a patient, the instructions comprising:
  using an imagery system to create an images dataset representing the amount of tissue connecting the inner and outer plexiform layers in the retina;
  measuring the amount of tissue connecting the inner and outer plexiform layers in the retina from the images dataset;
  determining if the amount of tissue measured is within a predetermined range; and
  if the amount of tissue measured is within the predetermined range, outputting a display image representing the presence of visual acuity in the retina of the patient.

23. The computer program product as claimed in claim 22, wherein said instructions cause said computer to derive measurements made in a series of concentric rings of different radii surrounding the fovea from said dataset.

24. The computer program product as claimed in claim 23, wherein said instructions cause said computer to determine the amount of said tissue in a region lying between 1000 and 2000 microns from the fovea.

25. The computer program product as claimed in claim 22, wherein said instructions cause the computer to obtain measurements from said dataset in a plane shaped to follow the contour of a predefined surface.

26. The computer program product as claimed in claim 25, wherein said predefined surface is the retinal surface or retinal pigment epithelium layer.

* * * * *